United States Patent [19]

Bron

[11] Patent Number: 4,796,660
[45] Date of Patent: Jan. 10, 1989

[54] DRIP EMITTER

[75] Inventor: Dan Bron, Haifa, Israel

[73] Assignee: Manisa Establishment, Zurich, Switzerland

[21] Appl. No.: 21,494

[22] Filed: Mar. 4, 1987

[30] Foreign Application Priority Data

Mar. 5, 1986 [IL] Israel .......................................... 78045

[51] Int. Cl.$^4$ .............................................. F16K 17/32
[52] U.S. Cl. ...................................... 137/504; 138/42; 138/45; 138/46; 239/542
[58] Field of Search ................... 137/504, 501; 138/42, 138/43, 45, 46; 239/542

[56] References Cited

U.S. PATENT DOCUMENTS

| | | | |
|---|---|---|---|
| 2,149,673 | 3/1939 | Godfrey | 137/504 X |
| 4,084,749 | 4/1978 | Drori | 138/42 X |
| 4,161,291 | 7/1979 | Bentley | 239/542 |
| 4,241,757 | 12/1980 | Bron | 137/501 |
| 4,428,397 | 1/1984 | Bron | 137/504 |
| 4,513,777 | 4/1985 | Wright | 137/504 X |

FOREIGN PATENT DOCUMENTS 487668 12/1953 Italy ..................................... 137/501

Primary Examiner—Martin P. Schwadron
Assistant Examiner—Stephen M. Hepperle
Attorney, Agent, or Firm—Saidman, Sterne, Kessler & Goldstein

[57] ABSTRACT

A flow-regulated drip emitter, including a housing provided with an inlet connector connectable into a relatively high-pressure liquid-line and an outlet opening, a flexible diaphragm retained along a peripheral portion thereof in the housing and dividing the interior of the housing into an inlet chamber and an outlet chamber, a flow-regulating valve comprised of a valve head accessible to the high pressure and a valve stem one end of which is attached to the valve head. The emitter further includes at least one flow-attenuating element disposed in the path of the liquid flowing from the inlet chamber into the outlet chamber, a valve seat associated with the valve head and located in a high-pressure region upstream of the inlet chamber, the valve seat and the valve head defining between them a gap through which the liquid passes on its way from the high-pressure line into the inlet chamber. The valve head is adapted to be acted upon by a first force tending to reduce the gap, and by a second force tending to increase the gap, a state of equilibrium between the forces defining the set point of the flow-regulated emitter.

9 Claims, 3 Drawing Sheets

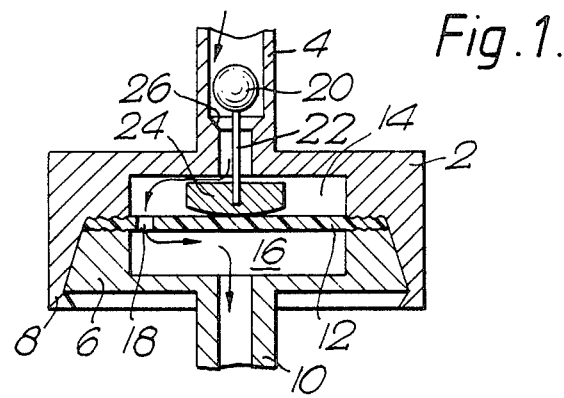
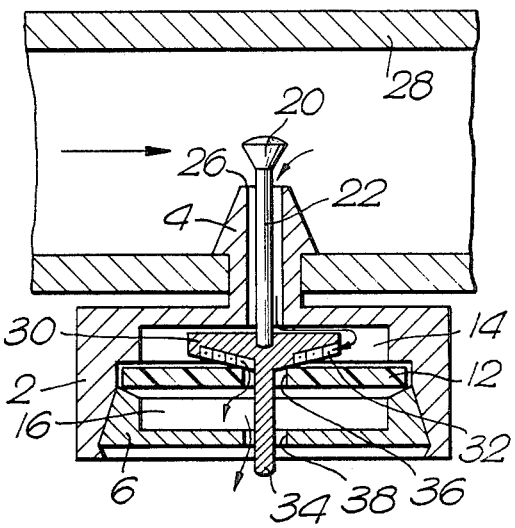
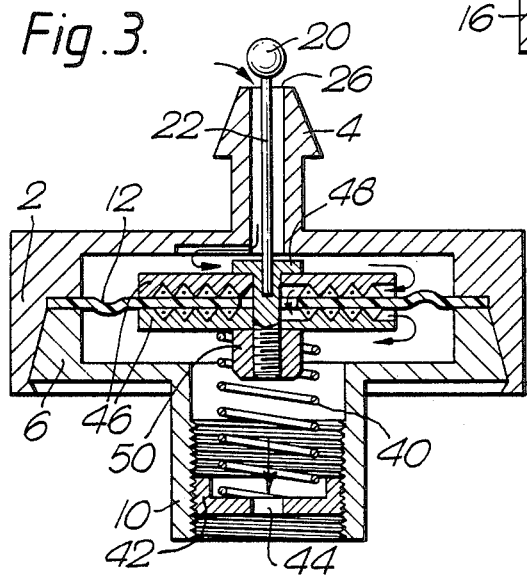

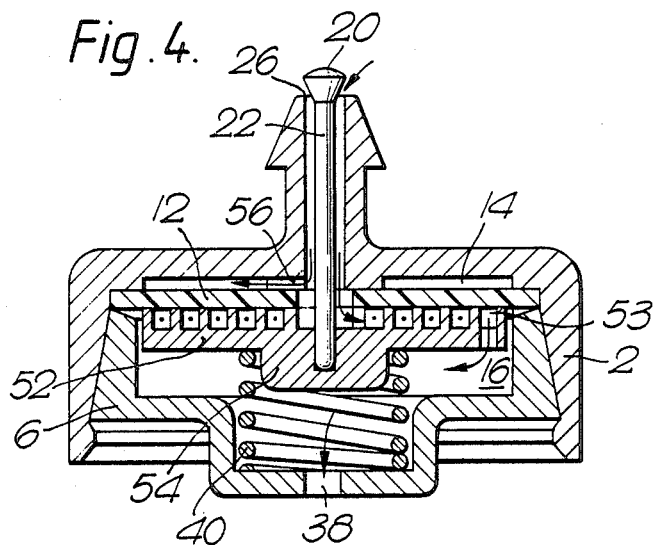
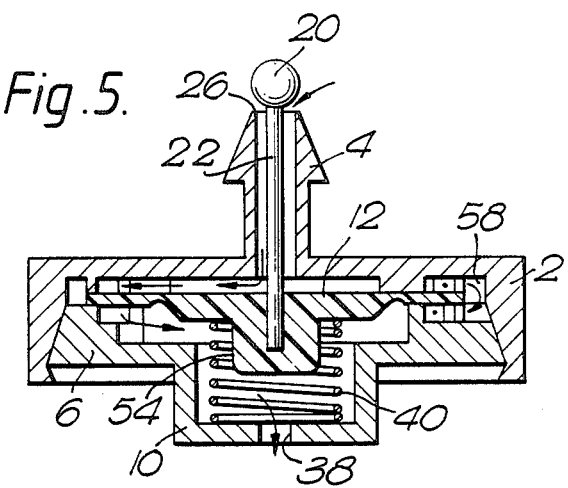
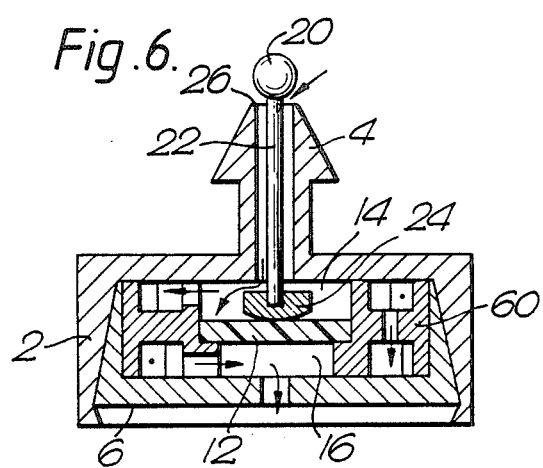

DRIP EMITTER

The present invention relates to a drip emitter, more particularly to a flow-regulated emitter for drip irrigation.

Experience in the field, extending over more than a decade, has shown that the many advantages of the flow-regulated drip-irrigation emitter are at least partly offset by the fact that, regulation taking place at the low-pressure outlet opening, the emitter is liable to act as a "dirt trap", filtering out all the solid impurities from the irrigation water and rapidly becoming clogged. In spite of the various improvements introduced in recent years with the aim of remedying this situation, the fact remains that as far as the ability to resist clogging is concerned, the flow-regulated emitter has so far been greatly inferior to the conventional, non-regulated emitter.

Another distinct disadvantage of the flow-regulated emitter is due to the fact that, regulation, as already mentioned, being effected must be able to withstand full line pressure, a circumstance which not only causes serious sealing problems, but also requires the use of relatively costly high-strength materials.

It is one of the objects of the present invention to overcome the drawbacks and disadvantages of prior-art flow-regulated emitters, and to provide a flow-regulated emitter that, while retaining the well-known advantages of these emitters, is largely non-clogging and can be manufactured from relatively cheap materials, as line pressure is excluded from the interior of the emitter.

This the invention achieves by providing a flow-regulated drip emitter, comprising:

a housing provided with an inlet connector connectable into a relatively high-pressure liquid-line, and an outlet opening;

a flexible diaphragm retained along a peripheral portion thereof in said housing and dividing the interior of said housing into an inlet chamber and an outlet chamber;

a flow-regulating valve comprised of a valve head accessible to said high pressure and a valve stem one end of which is attached to said valve head;

at least one flow-attenuating element disposed in the path of said liquid flowing from said inlet chamber into said outlet chamber;

a valve seat associated with said valve head and located in a high-pressure region upstream of said inlet chamber, said valve seat and said valve head defining between them a gap through which the liquid passes on its way from said high-pressure line into said inlet chamber, wherein said valve head is adapted to be acted upon by a first force tending to reduce said gap, and by a second force tending to increase said gap, a state of equilibrium between said forces defining the set point of said flow-regulated emitter.

The invention will nowwbe described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the Figures:

FIG. 1 shows a first embodiment of the emitter according to the invention, having a clamped diaphragm with an eccentrically located opening for flow attenuation;

FIG. 2 shows a second embodiment, in which the diaphragm is freely seated between the two housing halves and which is flushable;

FIG. 3 represents a third embodiment with an adjustable spring as reference force and two labyrinth disks clamping the diaphragm between them;

FIG. 4 shows a fourth embodiment with a spring as reference force and a labyrinth disk contacting the diaphragm from below;

FIG. 5 illustrates a fifth embodiment, having a spring as reference force and a labyrinth as integral part of the two housing halves;

Figure 7:
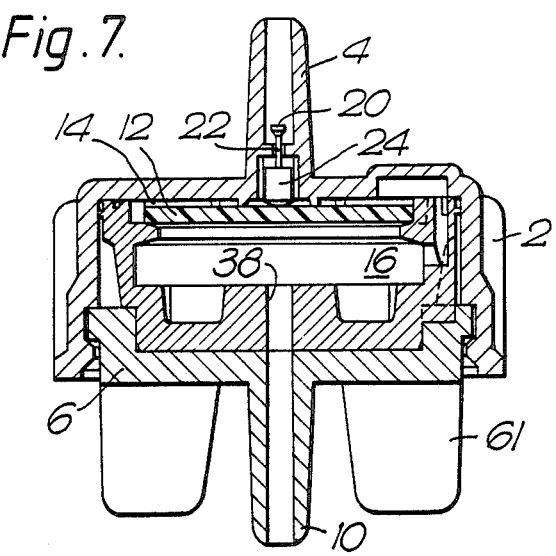
Figure 8:
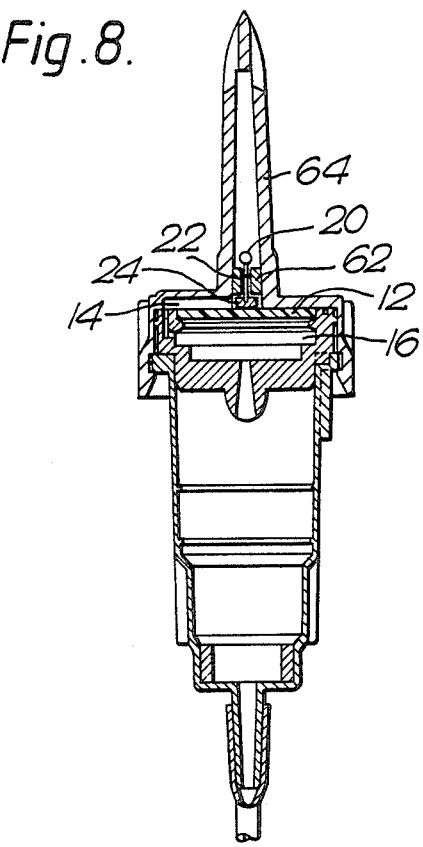

FIG. 6 shows a sixth embodiment, in which the labyrinth is provided in a separate member, in a recess of which freely rest the diaphragm, and FIG. 7 represents an embodiment of the emitter according to the invention, the flow rate of which is adjustable, and FIG. 8 represents an adjustable-rate, constant output infusion set having the same flow-regulating elements as are used in the emitters according to the invention.

There is shown in FIG. 1 a first embodiment of the emitter according to the invention. Seen is a two-part housing, the upper part 2 of which is provided with an inlet connector 4, here in the form of a tubular protrusion connectable to a water supply of relatively high pressure. The lower housing part 6 is attached to the upper part 2 by means of, e.g., a snap-in joint 8 and is provided with an outlet opening in the form of a tubular socket 10. Between the two housing parts 2 and 6 is held by clamping action along its periphery a flexible, elastically deformable diaphragm 12, which divides the interior of the housing into an inlet chamber 14 and an outlet chamber 16. The diaphragm 12 is provided with a relatively small, eccentrically located opening 18 which, in a manner to be explained further below, serves as flow-attenuating element.

There is further provided a valve assembly comprised of a valve head 20, spherical in this particular embodiment, and carried by a valve stem 22, to the free end of which is attached a pad 24 freely resting on the diaphragm 12. Further seen is a chamber-like, annular surface which serves as valve seat 26 to the valve head 20. The latter, as is obvious from FIG. 1, is always accessible to the high pressure of the supply line.

FIG. 1 shows the emitter in the empty state, in which the valve head, supported by the—at this stage—substantially flat diaphragm, is lifted clear off the valve seat 26. When now the water supply is turned on, water at the relatively high supply-line pressure starts to flow via the imlet connector 4 through the annular gap between valve head 20 and valve seat 26 first into the inlet chamber 14 and then, via the flow-attenuating opening 18, into the outlet chamber. The resistance offered by the relatively small opening 18 produces a perceptible pressure drop between the inlet and outlet chamber. This pressure drop or differential pressure causes the diaphragm 12 to bulge downward (by elastically stretching), thereby also permitting the valve assembly (pad 26, stem 22 and head 20) to drop relative to the emitter housing. As a consequence of this, the valve head 20 approaches the valve seat 26, the above-mentioned gap is reduced and inflow into the inlet chamber 14 is progressively diminished. Since at the same time outflow through the outlet socket 10 continues, pressure in the inlet chamber 14 drops, and differential pressure, i.e., the difference between the pressures in the two chambers 14 and 16, drops, too. This enables the natural elasticity of the diaphragm 12 to reduce the bulge produced by the previously high differential pressure. Now, a reduction of the bulge, that is, a flattening of the diaphragm will obviously cause the valve assembly to be raised, thereby again enlarging the gap between valve head 20 and valve seat 26, and thus increase inflow, starting the above-described cycle again. A state of equilibrium is eventually achieved, when the bulging force, i.e., the differential pressure, and the restoring force, i.e., the resilience of the diaphragm become substantially equal. This state defines the so-called set point of this flow-regulating system which makes emitter output largely independent of line pressure and its fluctuations.

In actual operation of the drip irrigation emitter according to the invention, the gap slightly oscillates about a width of less than 0.1 mm, which explains the filtering effect of the emitter according to the invention: solid particles of a size that in prior-art flow regulated emitters will cause clogging, are simply not admitted by the 0.1-mm-gap. Particles smaller than 0.1 mm will harmlessly pass through all types of flow-attentuating elements, such as the opening 18 in the presently discussed embodiment, or the various types of labyrinths in the embodiments explained further below.

In FIG. 2 the principle of non-clogging flow regulation as explained in conjuction with FIG. 1 is applied to a flushable emitter, otherwise similar to those disclosed in the co-pending Israel Application No. 76642. The inlet connector 4 in this embodiment, as also in the embodiments of FIGS. 3 to 6, is in the form of a "barbed" tubular projection that, once pressed into a pre-punched hole in the supply line 28, stays "hooked" and provides a permanent, secure and water-tight connection.

The valve assembly in this embodiment consists of the valve head 20, conical in this case, the valve stem 22, a disk-like member 30 which is the analogue of the pad 24 of FIG. 1, but also carries the flow-attenuating elements 32 known from the above-mentioned application as guide grooves 22, and a push rod 34 to initiate the flushing action as explained in the above application. The valve seat 26 in this embodiment is constituted by the edge of the bore of the inlet connector 4. It is clearly seen that in this, as well as in the following embodiments, in which the valve seat and head reach directly into the supply line 28, any dirt not admitted by the narrow working gap, but still somehow clinging to the valve head 20 is simply swept away by the flow in the supply line.

As in FIG. 1, the flow path of the irrigation water is indicated by arrows.

In this embodiment, the diaphragm 12 is not clamped tight along its periphery, but is freely seated in a recess between the two housing halves 2 and 6, and has a central hole 36 which serves merely to admit the push rod 34 and as a passageway for the water exiting the innermost of the flow-attenuating elements 32 and about to enter the outlet chamber 16, whence it reaches the atmosphere via a bore 38 in the lower housing member 6.

The flow-regulating action of this embodiment is completely analogous to that of the previous embodiment, except that the bias or reference force is now the resistance of diaphragm 12 to bending and not to stretching, as was the case with the clamped diaphragm of FIG. 1. For this reason the freely seated diaphragms of FIGS. 2, 6 and 7 are of a greater thickness than those that are clamped and bulge by stretching.

In the embodiment of FIG. 3, the diaphragm, though clamped along its periphery between the housing halves 2 and 6, is relatively slack and serves only as a partition separating the inlet chamber 14 from the outlet chamber 16, but not as the bias or restoring force as was the case in the embodiments of FIGS. 1 and 2. This task is here performed by a helical spring 40 mounted in the internally threaded outlet socket 10. The spring 40 bears at its lower end against an adjustable end plate 42 having a central outlet opening 44, and, at its upper end, against the lower one of two flow-attenuating elements in the shape of disks 46 between which the diaphragm 12 is clamped by means of a screw 48 and nut 50. Each disk is provided with a flow-attenuating, spiral-shaped, labyrinth which, in assembly, faces a diaphragm surface. The diaphragm 12 has a central hole through which the water, having passed through the labyrinth of the upper disk, enters the labyrinth of the lower disk. To the screw 48 is also attached the valve stem 22, and the nut 50 also serves as a guide and locator for the helical spring 40. Prestressing the latter to a greater or lesser extend by adjusting the end plate 42, the differential pressure, of which the spring 40 provides one component, can be varied, and thus also the emitter set point and, therefore, output.

The embodiment represented in FIG. 4 has a single flow-attenuating element somewhat similar to one of the disks 46 of the previous embodiment, consisting of a disk 52 having a spiral flow-attenuating labyrinth with an inlet in the center, and an outlet 53 at the periphery. The disk 52 is also provided with a central boss 54 which serves both for the attachment of the valve stem 22 and as guide and locator for the spiral spring 40 that, in analogy to the previous embodiment, is used as reference force.

The diaphragm 12 is not clamped along its periphery, but freely seated between the two housing halves 2 and 6. Line pressure which reaches the inlet chamber 14 through a lateral passage 56 keeps the diaphragm 12 always pressed against the spiral grooves of the labyrinth, thus preventing "short circuits" between adjacent grooves. As in the previous embodiment, the diaphragm 12 has a central hole through which water from the inlet chamber can reach the entrance of the labyrinth.

In the embodiment of FIG. 5, the labyrinth is of the two-tier meander type and extends over two annular zones, the upper tier being an integral part of the upper housing half 2, the lower tier, of the lower housing half 6. Except for the cross-over passage 58, the two tiers are separated by the peripheral portion of the diaphragm 12 which in this embodiment, too, acts as a partition between the two chambers and has also a central boss 54 which serves the same purpose as the boss 54 of the disk 52 of the previous embodiment. Here, too, a spring 40 serves as reference force.

The embodiment shown in FIG. 6 has a valve assembly similar to that of FIG. 1, with a pad 24 resting on the diaphragm 12. The latter, however, is of the non-clamped type and freely rests in a separate, annular flow-attenuating element 60 accommodated between the two housing halves 2 and 6. The element is of the meander-type labyrinth, arranged in two tiers, with the inlet in the upper tier and the exit at the lower tier. The reference force is supplied by the diaphragm 12.

It should be understood that the different elements in the various embodiments are largely interchangeable. Thus the springs 40 in the embodiments shown in FIGS. 3, 4 and 5 could well be replaced by diaphragms either clamped as in FIG. 1 or freely resting as in FIGS. 2 or 6; the diaphragm 12 in FIG. 6 could be of the clamped type, etc.

FIG. 7 represents an embodiment of the invention that is not only flow-regulated in the sense and manner of the previous embodiments, but has also a flow rate that is adjustable over a wide range. Once set to a given flow rate, this emitter will maintain that rate regardless of pressure fluctuations in the supply line. The manner in which the adjustable-rate feature of this embodiment functions is explained in conjunction with an infusion set disclosed in U.S. Pat. No. 4,343,305 and need not be gone into here. The flow-regulating feature, on the other hand, is the same as with the previous embodiments, comprising the valve assembly consisting of the valve head 20, the valve stem 22 and the pad 24 which rests on the diaphragm 12. The wing-like projections 61 integral with the lower housing part 6 facilitate a relative rotary movement between the upper and lower housing parts 2 and 6, by which, as explained in the above disclosure, flow-rate adjustment is effected.

FIG. 8 illustrates the use of the present invention in an adjustable flow rate infusion set of the type described in the above-mentioned disclosure. An inlet sleeve 62 is seen to have been introduced into the lower portion of the connector 64, to accommodate the valve assembly (head 20, stem 22 and pad 24).

It will be evident to those skilled in the art that the invention is not limited to the details of the foregoing illustrative embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A flow-regulated drip emitter, comprising:
    a housing provided with an inlet connector connectable to a relatively high-pressure liquid-line, and an outlet opening;
    a flexible disphragm retained along a peripheral portion thereof in said housing and dividing the interior of said housing into an inlet chamber and an outlet chamber;
    a flow-regulating valve comprised of a valve head accessible to said high presure and a valve stem one end of which is attached to said valve head;
    at least one flow-attenuating element disposed in the path of said liquid flowing from said inlet chamber to said outlet chamber;
    a valve seat associated with said valve head and located in a high-pressure region upstream of said inlet chamber, said valve seat and said valve head defining between them a gap through which the liquid passes on its way from said high-pressure line into said inlet chamber, said valve head being adapted to be acted upon by a first force tending to reduce said gap, and by a second force tending to increase said gap, a state of equilibrium between said forces defining the set point of said flow-regulated emitter.
    wherein said gap is fully exposed to liquid flow in said high-pressure line, wherein said flow-attenuating element is in the form of a labyrinth-type passageway, at least one liquid-contacting, active wall of said flow-attenuating element being constituted by said flexible diaphragm, and
    wherein the maximum opening size of said gap defined by said valve head and said valve seat is smaller than the maximum opening provided in aid labyrinth-type passaageway.

2. The emitter as claimed in claim 12, wherein said labyrinth-type passageway is in the form of at least one spiral duct.

3. The emitter as claimed in claim 1, wherein said second force is provided by a helical compression spring.

4. The emitter as claimed in claim 1, wherein said labyrinth-type passageway is in the form of at least one meandering duct.

5. The emitter as claimed in claim 1, further comprising a contact pad attached to a free end of said valve stem and adapted to be pushed by said flexible diaphragm.

6. The emitter as claimed in claim 1, further comprising at least one rigid disk-like member attached to a free end of said valve stem and provided on one of its surfaces with at least one of said labyrinth-type passageways.

7. The emitter as claimed in claim 6, wherein said flexible diaphragm is in permanent contact with the labyrinth-type passageway carrying surface of said disk like member;

8. The emitter as claimed in claim 6, wherein said flexbile diaphragm is clamped between two of said disk-like members, the labyrinth-type passageway of which members face respective surfaces of said flexible diaphragm.

9. The emitter as claimed in claim 1, wherein said second force is provided by said flexible diaphragm resisting change of shape.

* * * * *